United States Patent [19]

Schmidt et al.

[11] 4,283,077

[45] Aug. 11, 1981

[54] INDOLE COLOR FORMER

[75] Inventors: Paul J. Schmidt, Sharonville; William M. Hung, Cincinnati, both of Ohio

[73] Assignee: Sterling Drug Inc., New York, N.Y.

[21] Appl. No.: 127,649

[22] Filed: Mar. 6, 1980

[51] Int. Cl.³ .................... B41M 5/16; B41M 5/18; B41M 5/22
[52] U.S. Cl. .................... 282/27.5; 260/326.15; 260/326.16; 427/151; 428/307; 428/537; 428/913; 428/914; 430/200; 430/348; 430/964
[58] Field of Search .................... 260/319.1, 326.12 R, 260/326.15, 326.16; 282/27.5; 427/151; 428/307, 411, 537, 913, 914; 430/200, 348, 964

[56] References Cited

U.S. PATENT DOCUMENTS

| | | | |
|---|---|---|---|
| 3,957,288 | 5/1976 | Lemahieu et al. | 282/27.5 |
| 3,995,088 | 11/1976 | Garner et al. | 282/27.5 |
| 4,072,690 | 2/1978 | Garner et al. | 260/326.15 |
| 4,089,546 | 5/1978 | Petitpierre | 282/27.5 |
| 4,124,227 | 11/1978 | Ruus | 282/27.5 |

*Primary Examiner*—Bruce H. Hess
*Attorney, Agent, or Firm*—Paul E. Dupont; B. Woodrow Wyatt

[57] ABSTRACT

Aldehyde or ketone 0-[(3-indolyl)(aryl or heteroaryl)-methyl]oximes which are useful as color-formers in pressure-sensitive carbonless duplicating systems and thermal marking systems are prepared by reacting 3-[(arylsulfonyl)(aryl or heteroaryl)methyl]-1H-indoles with aldehyde or ketone oximes in the presence of a base.

3 Claims, No Drawings

INDOLE COLOR FORMER

BACKGROUND OF THE INVENTION

1. Field of the Invention

The present invention relates to a group of compounds classified in the field of organic chemistry as aldehyde or ketone O-[(3-indolyl)(aryl or heteroaryl)-methyl]oximes which are useful as color formers in pressure-sensitive carbonless duplicating systems and thermal marking systems; to processes for the preparation thereof and to pressure-sensitive carbonless duplicating systems and thermal marking systems containing the same.

2. Description of the Prior Art

Several classes of organic compounds of widely diverse structural types are known to be useful as color formers for carbonless duplicating systems. Among the most widely recognized classes are the phenothiazines, for example, benzoyl leuco methylene blue; fluorans, for example, 2'-anilino'6'-diethylaminofluoran; phthalides, for example, crystal violet lactone; methine dyes, for example, Michler's hydrol and derivatives thereof and various other types of color formers currently employed in commercially accepted carbonless duplicating systems. Typical of the many such systems taught in the prior art are those described in U.S. Pat. Nos. 2,712,507, 2,800,457 and 3,041,289, which issued July 5, 1955, July 23, 1957 and June 26, 1962, respectively. Many of the color formers in the prior art suffer one or more disadvantages such as low tinctorial strength, poor light stability, poor xerographic copiability, low resistance to sublimation limation and low solubility in common organic solvents, the latter disadvantage thus requiring the use of specialized and expensive solvents in order to obtain microencapsulated solutions of sufficient concentration for use in pressure-sensitive copying systems.

The most pertinent prior art relative to the present invention appears to be U.S. Pat. No. 4,124,227 issued Nov. 7, 1978 which discloses oxime ethers of Michler's hydrol as color precursors in pressure-sensitive copying systems.

SUMMARY OF THE INVENTION

The present invention provides certain novel aldehyde or ketone 0-[(1-$R_1$-2-$R_2$-1H-indol-3-yl) (Z)methyl]oximes alternatively named as 1-$R_1$-2-$R_2$-3-[($R_3R_4C$=NO)(Z)methyl]-1H-indoles which are useful as color formers in pressure-sensitive carbonless duplicating systems and thermal marking systems. The compounds develop colored images of good tinctorial strength and have the advantage of good xerographic copiability and enhanced solubility in common organic solvents.

This invention also provides a novel process for preparing the above-described O-(substituted methyl)oximes which comprises reacting a 1-$R_1$-2-$R_2$-3-[(R-phenylsulfonyl)(Z)methyl]-1H-indole with an oxime $R_3R_4C$=NOH in the presence of an alkali metal hydroxide.

The invention further provides as an article of manufacture a pressure-sensitive carbonless duplicating system or thermal marking system which contains a support sheet coated with a color-forming substance comprising an aldehyde or ketone 0-[(1-$R_1$-2-$R_2$-1H-indol-3-yl)(Z)methyl]oxime.

DETAILED DESCRIPTION OF THE INVENTION INCLUSIVE OF THE PREFERRED EMBODIMENTS

More specifically the invention sought to be patented resides in a composition of matter aspect in aldehyde or ketone 0-[(1-$R_1$-2-$R_2$-1H-indol-3-yl)(Z)methyl]oximes alternatively designated as 1-$R_1$-2-$R_2$-3-[($R_3R_4C$=NO)(Z)methyl]-1H-indoles which are useful as color formers in pressure-sensitive carbonless duplicating systems and thermal marking systems and which have Formula I

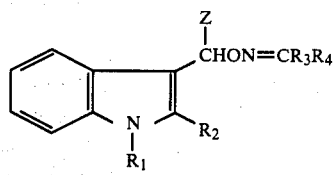

Formula I wherein:
$R_1$ is hydrogen or lower-alkyl;
$R_2$ is hydrogen, lower-alkyl or phenyl;
$R_3$ and $R_4$ are independently hydrogen, alkyl containing 1-8 carbon atoms, benzyl, phenyl, phenyl substituted with 1 or 2 halo, lower-alkyl, lower-alkoxy or di-lower-alkylamino groups, or $CR_3R_4$ is cyclopentyl, cyclohexyl or cycloheptyl, provided that $R_3$ and $R_4$ are not simultaneously hydrogen; and
Z is naphthyl, biphenylyl, phenyl, phenyl substituted with 1 or 2 lower-alkyl, lower-alkoxy, halo or nitro groups or Z is a substituent having the formula

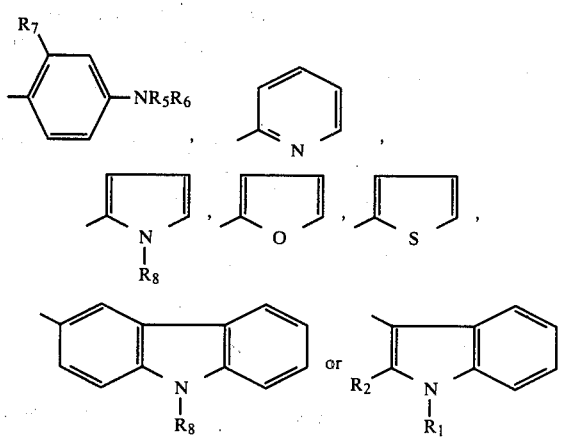

where in the above formulas
$R_5$ and $R_6$ are independently lower-alkyl or benzyl;
$R_7$ is hydrogen, lower-alkyl, lower-alkoxy, halo or di-lower-alkylamino, and
$R_8$ is hydrogen or lower-alkyl.

Preferred embodiments of this invention are compounds of Formula I hereinabove wherein $R_1$, $R_2$, $R_3$ and $R_4$ have the previously given meanings and Z is a substituent having the formula

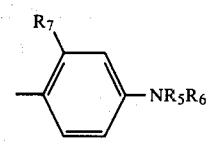

where $R_5$, $R_6$ and $R_7$ have the above given meanings. Particularly preferred are those compounds wherein $R_5$ and $R_6$ are each lower-alkyl and $R_7$ is hydrogen. These compounds are especially valuable because they are obtained from inexpensive and readily available starting materials.

In an article of manufacture aspect the invention sought to be patented resides in a pressure-sensitive carbonless duplicating system or thermal marking system containing a support sheet coated with a color-forming substance comprising a compound having Formula I hereinabove wherein $R_1$, $R_2$, $R_3$, $R_4$ and $Z$ have the previously given meanings.

Preferred pressure-sensitive carbonless duplicating systems or thermal marking systems of the present invention are those which contain a color-forming substance comprising one of the above-described preferred compounds, that is, a compound of Formula I wherein $R_1$, $R_2$, $R_3$ and $R_4$ have the previously given meanings and $Z$ is a substituent having the formula

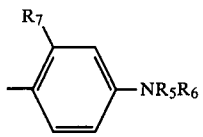

particularly where $R_5$ and $R_6$ are each lower-alkyl and $R_7$ is hydrogen.

In its process aspect the invention sought to be patented resides in a process for producing a compound having Formula I which comprises reacting a compound having Formula II

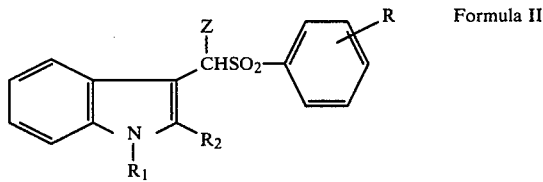
Formula II with an oxime having Formula III

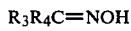
$R_3R_4C=NOH$    Formula III in the presence of an alkali metal hydroxide, where in the above formulas R is hydrogen or lower-alkyl;
$R_1$ is hydrogen or lower-alkyl;
$R_2$ is hydrogen, lower-alkyl or phenyl;
$R_3$ and $R_4$ are independently hydrogen, alkyl containing 1 to 8 carbon atoms, benzyl, phenyl, phenyl substituted with 1 or 2 halo, lower-alkyl, lower-alkoxy or di-lower-alkylamino groups, or $CR_3R_4$ is cyclopentyl, cyclohexyl or cycloheptyl, provided that $R_3$ and $R_4$ are not simultaneously hydrogen; and
Z is naphthyl, biphenylyl, phenyl, phenyl substituted with 1 or 2 lower-alkyl, lower-alkoxy, halo or nitro groups or Z is a substituent having the formula

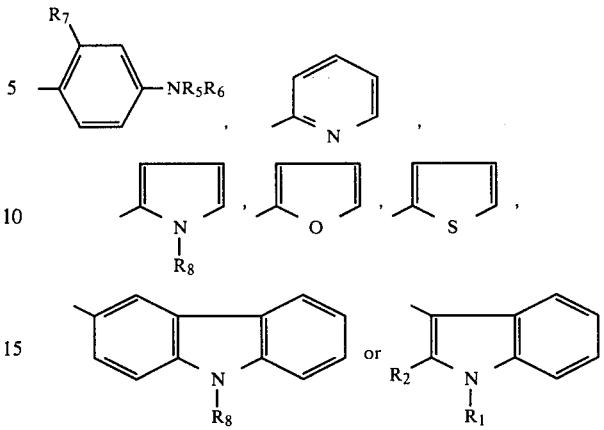

where in the above formulas
$R_5$ and $R_6$ are independently lower-alkyl or benzyl;
$R_7$ is hydrogen, lower-alkyl, lower-alkoxy, halo or di-lower-alkylamino, and
$R_8$ is hydrogen or lower-alkyl.

As used herein the terms "lower-alkyl", "lower-alkoxy" and "di-lower-alkylamino-" denote saturated acyclic groups having from 1 to 4 carbon atoms which may be straight or branched as exemplified by methyl, ethyl, propyl, isopropyl, butyl, sec-butyl, isobutyl, t-butyl, methoxy, ethoxy, propoxy, isopropoxy, butoxy, sec-butoxy, isobutoxy, t-butoxy, dimethylamino, diethylamino, ethylmethylamino, dipropylamino, dibutylamino, isobutylmethylamino, t-butylmethylamino and the like.

As used herein "halo" is intended to include chloro, fluoro, bromo and iodo and "alkali metal hydroxide" includes lithium, sodium and potassium hydroxide.

The novel compounds of Formula I hereinabove are essentially colorless in the depicted form. When contacted with an acidic medium, for example silica gel or one of the types ordinarily employed in pressure-sensitive carbonless duplicating systems such as silton clay or phenolic resin, the compounds of Formula I develop a yellow to purple image of good to excellent tinctorial strength and possess excellent xerographic copiability and enhanced solubility in common organic solvents. The compounds are thus highly suitable for use as colorless precursors, that is, color-forming substances in pressure-sensitive carbonless duplicating systems. Compounds producing a purple color can be used alone as color formers to produce images which are readily copiable whereas the compounds which produce a yellow to red color can be used as toners in admixture with other color formers to produce images of a neutral shade which desirably are readily copiable by xerographic means.

The compounds of this invention may be incorporated in any of the commercially accepted systems known in the carbonless duplicating art. A typical technique for such application is as follows: solutions containing one or more colorless precursor compounds of Formula I optionally in admixture with other color formers in suitable solvents are microencapsulated by well-known procedures, for example, as described in U.S. Pat. Nos. 3,649,649, 3,429,827 and 4,000,087. The microcapsules are coated on the reverse side of a transfer sheet with the aid of a suitable binder. The coated transfer sheet is then assembled in a manifold with the microcapsule-coated side in contact with a receiving sheet coated with an electron accepting substance, for example silton clay or phenolic resin. Application of pressure to the manifold such as that exerted by a stylus, typewriter or other form of writing or printing, causes the capsules on the reverse side to rupture. The solution of the color former released from the ruptured microcapsules flows to the receiving sheet and on contact with the acidic medium thereon forms a yellow to purple image of good tinctorial strength. It is, of course, obvious that variants of this mode of application can be utilized, for example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formula I are intimately mixed with an acidic developer of the type generally employed in thermal papers, for example bisphenol A, as described in U.S. Pat. No. 3,539,375, that is, papers which produce a colored image when contacted with a heated stylus or heated type, heating of the mixture produces a colored image of varying shades from yellow to purple, depending on the particular compound of the invention employed. The ability of the compounds of Formula I to form a deep color when heated in admixture with an acidic developer such as bisphenol A makes them useful in thermal paper marking systems either where an original or a duplicate copy is prepared by contacting the thermal paper with a heated stylus or a heated type in any of the methods generally known in the art.

In accordance with the aforementioned process aspect of this invention 1-$R_1$-2-$R_2$-3-[($R_3R_4C=NO$)(Z)methyl]-1H-indoles of Formula I are obtained by reacting approximately equimolar amounts of a R-phenylsulfonyl compound of Formula II and an oxime of Formula III in the presence of an alkali metal hydroxide at a temperature of about 0°–100° C. for approximately 1 to 60 hours. The reaction is conveniently carried out in the presence of aqueous potassium hydroxide at about 5°–25° C. for approximately 3 to 48 hours.

A 1-$R_1$-2-$R_2$-3-[($R_3R_4C=NO$)(Z)methyl]-1H-indole obtained in accordance with the above process can be isolated by filtration if it is insoluble in the reaction medium or by dilution of the reaction medium with a miscible solvent in which the product is insoluble such as water in order to effect precipitation of the product. Alternatively, the reaction mixture can be poured into water and the product extracted with an organic solvent such as benzene or toluene followed by evaporation of the organic solvent leaving the product as a residue. The product when it is isolated can be purified by conventional means such as trituration or recrystallization from a suitable solvent.

The 3-[(R-phenylsulfonyl)(Z)methyl]-1H-indoles of Formula II which are required as starting materials in the above-described process are obtained by reacting approximately equimolar amounts of an appropriate 1-$R_1$-2-$R_2$-1H-indole, an appropriate aldehyde Z-CHO and an R-phenylsulfinic acid (R, $R_1$, $R_2$ and Z having the previously given meanings) in the presence of an acid catalyst such as hydrochloric acid, in a suitable solvent, for example, N,N-dimethylformamide, or a lower-alkanol such as methanol, ethanol or 2-propanol at a temperature of about 5°–150° C. for approximately 1 to 35 hours. The reaction is usually carried out in ethanol at about 5°–60° C. for approximately 1 to 4 hours. The product thus obtained can be isolated by filtration if it is insoluble in the reaction medium or by the addition of a basic substance for example, triethanolamine or ammonium hydroxide to effect precipitation of the product. Alternatively, the reaction mixture can be poured into water or a dilute aqueous base, for ammonium hydroxide, sodium hydroxide, sodium carbonate or sodium bicarbonate and the product extracted with an organic solvent, such as benzene, chlorobenzene or toluene followed by evaporation of the organic solvent leaving the product as a residue. The product, once isolated, can be purified by conventional means such as trituration, recrystallization or slurrying in a suitable organic solvent.

The 1-$R_1$-2-$R_2$-1H-indoles as well as the aromatic or heterocyclic aldehydes Z-CHO which are starting materials for preparing the 3-[(R-phenylsulfonyl)(Z)methyl]-1H-indoles of Formula II constitute well-known classes of compounds many of which are commercially available or readily obtained by conventional syntheses well known in the art.

The R-phenylsulfinic acids which are also required as starting materials for the intermediates of Formula II likewise belong to an old and well-known class of compounds. Sulfinic acids are known to be unstable and cannot be stored for long periods of time. Accordingly, in the above-described reaction the sulfinic acid is generated in situ by acidifying an alkali metal R-phenylsulfinate which in turn is readily obtained by conventional procedures, for example, by reacting a R-phenylsulfonyl chloride with sodium sulfite and sodium bicarbonate in water. The sodium R-phenylsulfinate is stable and can be stored until needed. The R-phenylsulfonyl chlorides are, of course, readily available from the interaction of a R-phenylsulfonic acid or salt thereof with phosphorus oxychloride.

The oximes of Formula III are generally well-known and usually commercially available. If not available or if specifically new, a given oxime can be prepared from the corresponding well-known aldehyde or ketone according to conventional procedures.

The molecular structures of the compounds of this invention were assigned on the basis of the modes of synthesis and study of their infrared and nuclear magnetic resonance spectra.

The following examples will further illustrate the invention, without, however, limiting it thereto.

EXAMPLE 1

A. To a stirred mixture containing 175.0 ml. of ethyl alcohol, 27.5 ml. of concentrated hydrochloric acid, 30.4 g. of 86.4% sodium p-toluenesulfinate and 18.5 g. of p-(dimethylamino)benzaldehyde chilled to approximately 5° C. was slowly added 19.5 g. of 91.2% 1-ethyl-2-methyl-1H-indole. The resulting mixture was stirred approximately 3.5 hours at room temperature during which period the color changed from blue to yellow. The pH of the mixture was adjusted to approximately 8 by the addition of 40.0 g. of triethanolaine and after stirring approximately 20 minutes at room temperature the temperature was raised to and maintained at 55°–60° C. for approximately 20 minutes. After cooling to about 10° C. the resulting pink solid was collected by filtration and washed with 100 ml. of cold ethyl alcohol. The solid was then suspended in a mixture of 350 ml. of water and 10 g. of triethanolamine at room temperature for approximately 30 minutes, collected by filtration, washed successively with 150 ml. portions of 3% aqueous triethanolamine and water and dried under vacuum at 40° C. to give 42.2 g. of 3-{[4-(dimethylamino)phenyl](4-methylphenylsulfonyl)methyl}-1-ethyl-2-methyl-1H-indole which softened at 155° C. and melted at 159°–161° C.

B. To a stirred solution containing 2.7 g. (0.02 mole) of acetophenone oxime and 2.0 g. of potassium hydroxide in 100 ml. of acetone and 5 ml. of water was added 8.9 g. (0.02 mole) of 3-{[4-(dimethylamino)phenyl](4-methylphenylsulfonyl)methyl}-1-ethyl-2-methyl-1H-indole. After stirring twenty-four hours at room temperature, the solid which had formed was collected by filtration and washed with 50 ml. of 50% aqueous acetone. The solid was then washed with 35 ml. of isopropyl alcohol which caused some of the product to dissolve and reprecipitate in the filtrate. This material was isolated from the filtrate and recombined with the collected product to give 6.0 g. of acetophenone 0-{[4-(dimethylamino)phenyl](1-ethyl-2-methyl-1H-indol-3-yl)methyl}oxime which softened at 147° C. and melted at 148°–149.7° C. A toluene solution of this product when contacted with acidic clay or phenolic resin developed a red image.

EXAMPLE 2

Following a procedure similar to that described in Example 1B but employing 3.3 g. (0.02 mole) of 4-(dimethylamino)benzaldehyde oxime, 2.0 g. of potassium hydroxide and 8.9 g. (0.02 mole) of 3-{[4-(dimethylamino)phenyl](4-methylphenylsulfonyl)methyl}-1-ethyl-2-methyl-1H-indole in 80 ml. of acetone and 5 ml. of water, there was obtained following recrystallization from acetone, 1.6 g. of 4-(dimethylamino)benzaldehyde 0-{[4-(dimethylamino)phenyl](1-ethyl-2-methyl-1H-indol-3-yl)methyl}oxime, m.p. 184.5°–189.7° C. A toluene solution of this product when contacted with acidic clay or phenolic resin developed a reddish-purple image.

EXAMPLE 3

A. To a stirred mixture containing 5.0 ml. of concentrated hydrochloric acid, 35 ml. of ethyl alcohol, 6.2 g. of 85.9% sodium p-toluenesulfinate and 4.5 g. of 94.4% 1-ethyl-2-methyl-1H-indole was added 2.8 g. of thiophene-2-carboxaldehyde. After stirring approximately one hour at 55°–60° C. the reaction mixture was cooled to about 40° C. and then diluted with 25 ml. of ethyl alcohol followed by 300 ml. of water and 200 g. of ice. The resulting solid was collected by filtration and washed with water. The product was suspended in 60 ml. of cold 2-propanol containing sufficient ammonium hydroxide to maintain a slightly alkaline condition and the resulting suspension was stirred approximately 45 minutes at 5°–10° C. The solid was then collected by filtration, washed with fresh 2-propanol and dried under vacuum at 45° C. to afford 10.0 g. of 3-[(4-methylphenylsulfonyl)(2-thienyl)methyl]-1-ethyl-2-methyl-1H-indole, m.p. 168°–169° C. (dec.).

B. Following a procedure similar to that described in Example 1B but employing 3.3 g. (0.02 mole) of 4-(dimethylamino)benzaldehyde oxime, 2.0 g. of potassium hydroxide and 8.2 g. (0.02 mole) of 3-[(4-methylphenylsulfonyl)(2-thienyl)methyl]-1-ethyl-2-methyl-1H-indole in 80 ml. of acetone and 5 ml. of water, and stirring the reaction mixture about 40 hours at room temperature there was obtained 6.3 g. of 4-(dimethylamino)benzaldehyde 0-[(1-ethyl-2-methyl-1H-indol-3-yl)(2-thienyl)methyl]oxime, m.p. 136°–137° C. A toluene solution of this product when contacted with acidic clay or phenolic resin developed a yellow image.

EXAMPLE 4

Following a procedure similar to that described in Example 1B but employing 3.2 g. (0.02 mole) of 4-methoxybenzaldehyde oxime, 2.0 g. of potassium hydroxide and 8.2 g. (0.02 mole) of 3-[(4-methylphenylsulfonyl)(2-thienyl)methyl]-1-ethyl-2-methyl-1H-indole in 75 ml. of acetone and 5 ml. of water, and stirring the reaction mixture about 3 hours at room temperature, there was obtained 5.8 g. of 4-methoxybenzaldehyde 0-[(1-ethyl-2-methyl-1H-indol-3-yl)(2-thienyl)methyl]oxime, m.p. 138°–140.2° C. A toluene solution of this product when contacted with acidic clay or phenolic resin developed a yellow image.

EXAMPLE 5

To a solution containing 3.9 g. (0.02 mole) of benzophenone oxime and 2.0 g. of potassium hydroxide in 100 ml. of acetone and 5 ml. of water, was added 8.9 g. (0.02 mole) of 3-{[4-(dimethylamino)phenyl](4-methylphenylsulfonyl)methyl}-1-ethyl-2-methyl-1H-indole. The resulting solution was stirred about 28 hours at room temperature and then poured into 500 ml. of icewater. The resulting yellow solid was collected by filtration and then dissolved in a mixture of 100 ml. of isopropyl alcohol and 300 ml. of toluene. This solution was washed successively with 400 ml. each of water and saturated aqueous sodium chloride, and evaporated to dryness under vacuum to give 1.9 g. of benzophenone 0-{[4-(dimethylamino)phenyl](1-ethyl-2-methyl-1H-indol-3-yl)methyl}oxime as a dark brown oil. The NMR spectrum of this product was consistent with the expected structure and also indicated the presence of 1 mole of toluene. A toluene solution of this product when contacted with acidic clay or phenolic resin developed a reddish-purple image.

EXAMPLE 6

Following a procedure similar to that described in Example 5, but employing 2.3 g. (0.02 mole) of cyclohexanone oxime, 2.0 g. of potassium hydroxide and 8.9 g. (0.02 mole) of 3-{[4-(dimethylamino)phenyl](4-methylphenylsulfonyl)methyl}-1-ethyl-2-methyl-1H-indole in 100 ml. of acetone and 7 ml. of water, there was obtained 2.0 g. of cyclohexanone 0-{[4-(dimethylamino)phenyl](1-ethyl-2-methyl-1H-indol-3-yl)methyl}oxime as a dark green oil. A toluene solution of this product when contacted with acidic clay or phenolic resin developed a reddish-purple image.

EXAMPLE 7

A. Following a procedure similar to that described in Example 3A but employing 6.5 g. of 81.9% sodium p-toluenesulfinate, 2.4 g. of furfural and 3.8 g. of 86.1% of 1-ethyl-2-methyl-1H-indole, there was obtained 4.5 g. of 3-[(2-furyl)(4-methyl-phenylsulfonyl)methyl]-1-ethyl-2-methyl-1H-indole, m.p. 144°–146° C.

B. To a solution containing 3.9 g. (0.02 mole) of benzophenone oxime and 2.0 g. of potassium hydroxide in 75 ml. of acetone and 5 ml. of water was added 7.9 g. (0.02 mole) of 3-[(2-furyl)(4-methylphenylsulfonyl)methyl]-1-ethyl-2-methyl-1H-indole. After stirring for 24 hours at room temperature, the reaction mixture was partitioned between 300 ml. of toluene and 300 ml. of water. The toluene layer was separated, washed with saturated aqueous sodium chloride and evaporated under vacuum. The residue was crystallized from isopropyl alcohol and hexane to give 4.6 g. of benzophenone 0-[(1-ethyl-2-methyl-1H-indol-3-yl)(2-furyl)methyl]oxime, m.p. 113°–117° C. A toluene solution of this product when contacted with acidic clay or phenolic resin developed a yellow image.

EXAMPLE 8

Following a procedure similar to that described in Example 7, but employing 1.5 g. (0.02 mole) of acetone oxime, 2.0 g. of potassium hydroxide and 8.2 g. (0.02 mole) of 3-[(4-methylphenylsulfonyl)(2-thienyl)methyl]-1-ethyl-2-methyl-1H-indole in 100 ml. of acetone and 5 ml. of water, stirring the reaction mixture about 48 hours at room temperature and triturating the product with hexane, there was obtained 4.0 g. of acetone 0-[(1-ethyl-2-methyl-1H-indol-3-yl)(2-thienyl)methyl]oxime, m.p. 96.5°–104.5° C. A toluene solution of this product when contacted with acidic clay or phenolic resin developed a yellow-orange image.

EXAMPLE 9

Following a procedure similar to that described in Example 7, but employing 1.5 g. (0.02 mole) of acetone oxime, 2.0 g. of potassium hydroxide and 8.9 g. (0.02 mole) of 3-{[4-(dimethylamino)phenyl](4-methylphenylsulfonyl)methyl}-1-ethyl-2-methyl-1H-indole in 50 ml. of acetone, 5 ml. of water and 20 ml. of dimethylsulfoxide, and stirring the reaction mixture about 48 hours at room temperature, there was obtained 1.8 g. of acetone 0-{[4-(dimethylamino)phenyl](1-ethyl-2-methyl-1H-indol-3-yl)methyl}oxime which after recrystallization from isopropyl alcohol, had m.p. 180.5°–183.5° C. A toluene solution of this product when contacted with acidic clay developed a magenta image and when contacted with phenolic resin developed a violet image.

EXAMPLE 10

Following a procedure similar to that described in Example 7 but employing 3.3 g. (0.02 mole) of 4-(dimethylamino)benzaldehyde oxime, 2.0 g. of potassium hydroxide and 7.9 g. (0.02 mole) of 3-[(2-furyl)(4-methylphenylsulfonyl)methyl]-1-ethyl-2-methyl-1H-indole, there was obtained 3.9 g. of 4-(dimethylamino)benzaldehyde 0-[(1-ethyl-2-methyl-1H-indol-3-yl)(2-furyl)methyl]oxime which softened at 96° C. and melted at 99.8°–105.2° C. A toluene solution of this product when contacted with acidic clay or phenolic resin developed a yellow image.

EXAMPLE 11

To a stirred solution containing 3.9 g (0.02 mole) of benzophenone oxime and 2.0 g. of potassium hydroxide in 75 ml. of acetone and 5 ml. of water was added 8.2 g. (0.02 mole) of 3-[(phenylsulfonyl)(2-thienyl)methyl]-1-ethyl-2-methyl-1H-indole and the resulting mixture stirred overnight at room temperature. The reaction mixture was diluted with 75 ml. of water and stirred 0.5 hour. The product was collected by filtration, washed with aqueous acetone and dried at 48° C. under vacuum to give 8.6 g. of benzophenone 0-[(1-ethyl-2-methyl-1H-indol-3-yl)(2-thienyl)methyl]oxime, m.p. 141.3°–143.2° C. A toluene solution of this product when contacted with acidic clay or phenolic resin developed a yellow image.

EXAMPLE 12

Following a procedure similar to that described in Example 11 but employing 2.7 g. (0.02 mole) of acetophenone oxime, 2.0 g. of potassium hydroxide and 8.2 g. (0.02 mole) of 3-[(4-methylphenylsulfonyl)(2-thienyl)methyl]-1-ethyl-2-methyl-1H-indole in 75 ml. of acetone and 5 ml. of water, there was obtained 6.7 g. of acetophenone 0-[(1-ethyl-2-methyl-1H-indol-3-yl)(2-thienyl)methyl]oxime, m.p. 113°–115° C. A toluene solution of this product when contacted with acidic clay or phenolic resin developed a yellow image.

EXAMPLE 13

Following a procedure similar to that described in Example 11, but employing 3.2 g. (0.02 mole) of 4-methoxybenzaldehyde oxime, 2.0 g. of potassium hydroxide and 8.9 g. (0.02 mole) of 3-{[4-(dimethylamino)phenyl][(4-methylphenylsulfonyl)methyl]}-1-ethyl-2-methyl-1H-indole in 50 m. of acetone and 5 ml. of water, there was obtained 5.2 g. of 4-methoxybenzaldehyde 0-{[4-(dimethylamino)phenyl](1-ethyl-2-methyl-1H-indol-3-yl)methyl}oxime, m.p. 137.2°–139.7° C. A toluene solution of this product when contacted with acidic clay developed a magenta image and when contacted with phenolic resin developed a violet image.

It is contemplated that by following procedures similar to those described in the foregoing examples but employing the appropriate 1-$R_1$-2-$R_2$-3-[(R-phenylsulfonyl)(Z)methyl]-1H-indole and the appropriate oxime $R_3R_4C=NOH$ there will be obtained the 1-$R_1$-2-$R_2$-3-[($R_3R_4C=NO$)(Z)methyl]-1H-indoles of Formula I, Examples 14–30 presented in Table A hereinbelow.

TABLE A

| 1-$R_1$—2-$R_2$—3-[($R_3R_4C=NO$)(Z)methyl]-1H—indoles of Formula I | | | | | |
|---|---|---|---|---|---|
| Ex. | $R_1$ | $R_2$ | $R_3$ | $R_4$ | Z |
| 14 | H | $CH_3$ | H | $C_8H_{17}$ | 1-naphthyl |
| 15 | H | $C_6H_5$ | $CH_3$ | $(CH_3)_2CHCH_2$ | $C_6H_5$ |
| 16 | n-$C_4H_9$ | H | $CH_3$ | 4-Br—$C_6H_4$ | 4-$C_6H_5$—$C_6H_4$ |
| 17 | $CH_3$ | $CH_3$ | $CH_3$ | $C_6H_5CH_2$ | 2-$CH_3$—$C_6H_4$ |
| 18 | H | H | —$(CH_2)_4$— | | 3,4-$(CH_3O)_2$—$C_6H_3$ |
| 19 | H | $C_2H_5$ | —$(CH_2)_6$— | | 3-$NO_2$—$C_6H_4$ |
| 20 | $C_2H_5$ | $CH_3$ | $C_2H_5$ | 2,4-$(CH_3)_2$—$C_6H_3$ | 2-pyridinyl |
| 21 | H | $CH_3$ | n-$C_4H_9$ | n-$C_4H_9$ | 1-$CH_3$—2-pyrrolyl |
| 22 | $C_2H_5$ | $CH_3$ | $CH_3$ | $CH_3$ | 1-$C_2H_5$—2-$CH_3$—3-indolyl |
| 23 | $C_2H_5$ | $CH_3$ | $CH_3$ | $C_6H_5$ | 9-$C_2H_5$—carbazol-3-yl |
| 24 | $CH_3$ | H | $CH_3$ | 2,4-$(Cl)_2$—$C_6H_3$ | 4-Cl—$C_6H_4$ |
| 25 | $C_2H_5$ | $CH_3$ | H | $C_6H_{13}$ | 2,4-$[(CH_3)_2N]_2$—$C_6H_3$ |
| 26 | H | $CH_3$ | H | 3-F—$C_6H_5$ | 2-$C_2H_5O$—4-$(C_2H_5)_2N$—$C_6H_3$ |
| 27 | $CH_3$ | H | H | 3,4-$(CH_3O)_2$—$C_6H_3$ | 2-Cl—4-$(CH_3)_2N$—$C_6H_3$ |
| 28 | H | $CH_3$ | H | 2,4-$[(CH_3)_2N]_2$—$C_6H_3$ | 2-$CH_3$—4-$(CH_3)_2N$—$C_6H_3$ |
| 29 | $C_2H_5$ | H | $C_2H_5$ | $C_2H_5$ | 2-Br—4-$(CH_3)_2N$—$C_6H_3$ |

TABLE A-continued

1-R$_1$—2-R$_2$—3-[(R$_3$R$_4$C=NO)(Z)methyl]-1H—indoles of Formula 1

| Ex. | R$_1$ | R$_2$ | R$_3$ | R$_4$ | Z |
| --- | --- | --- | --- | --- | --- |
| 30 | C$_2$H$_5$ | CH$_3$ | CH$_3$ | CH$_3$ | $\underset{4-(C_6H_5CH_2N)-C_6H_4}{\overset{C_2H_5}{|}}$ |

EXAMPLE 31

The color former of Example 1 was microencapsulated and applied to a carbonate duplicating transfer sheet as follows: a solution prepared by dissolving 0.73 g. of the color former in 30 g. of isopropylbiphenyl at 55° C. and a solution prepared by slowly dissolving 2.5 g. of carboxymethylcellulose in 100 ml. of distilled water were mixed and emulsified by rapid stirring at 50° C. The desired particle size (1-2 microns) was checked by microscope. A solution prepared by dissolving 7.5 g. of pigskin gelatin in 60 ml. of distilled water at 50° C. followed by stirring approximately 1 hour at 50° C. was then added to the stirred emulsion and the pH was adjusted to 6.5 with 10% aqueous sodium hydroxide with rapid stirring. Following the gradual addition of 335 ml. of distilled water at 50° C. the pH was adjusted to 4.5 with 10% aqueous acetic acid with continued rapid stirring. After 5 minutes the mixture was cooled to 15° C. and 5 ml. of 25% aqueous glutaraldehyde was added dropwise while rapid stirring was continued an additional 15 minutes. After stirring more slowly overnight, the weight of the microcapsule dispersion was adjusted to 560 g. with distilled water to give a color former concentration of approximately 0.13%. White typewriter paper sheets (transfer sheets) were coated with this dispersion at a film thickness of 0.0015 inch and air-dried. The coated side of a transfer sheet was placed in contact with a receiving sheet coated with either phenolic resin or acidic clay. Typing on the transfer sheet produced a red-violet duplicate typewritten image on the receiving sheet.

EXAMPLE 32

The color former of Example 1 was incorporated in a thermal paper essentially according to the procedure described in U.S. Pat. No. 3,539,375. A polyvinyl alcohol dispersion of the color former of Example 1 was prepared by shaking one hour on a paint shaker a mixture containing 2.0 g. of color former, 3.7 g. of water, 8.6 g. of 10% aqueous polyvinyl alcohol and 10 ml. of zirconium grinding beads. A polyvinyl alcohol dispersion of bisphenol A was prepared by shaking a mixture containing 9.8 g. of bisphenol A, 18.2 g. of water, 42 g. of 10% aqueous polyvinyl alcohol and 70 ml. of zirconium grinding beads. The coating mixture was made by combining and thoroughly mixing 2.1 g. of the polyvinyl alcohol dispersion of the color former with 47.9 g. of the polyvinyl alcohol dispersion of bisphenol A. The coating mixture was applied at a thickness of 0.0015 inch to white paper sheets and the sheets were dried at room temperature. Contacting the coated sheets with a heated stylus at temperatures between 100° C. and 150° C. produced a deep purple to dark blue-purple image.

We claim:

1. A pressure-sensitive carbonless duplicating system or thermal marking system containing a support sheet coated with a color-forming substance comprising a compound having the formula

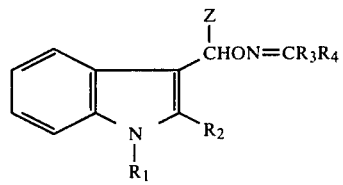

wherein:
R$_1$ is hydrogen or lower-alkyl;
R$_2$ is hydrogen, lower-alkyl or phenyl;
R$_3$ and R$_4$ are independently hydrogen, alkyl containing 1-8 carbon atoms, benzyl, phenyl, phenyl substituted with 1 or 2 halo, lower-alkyl, lower-alkoxy or di-lower-alkylamino groups, or CR$_3$R$_4$ is cyclopentyl, cyclohexyl or cycloheptyl, provided that R$_3$ and R$_4$ are not simultaneously hydrogen; and
Z is naphthyl, biphenylyl, phenyl, phenyl substituted with 1 or 2 lower-alkyl, lower-alkoxy, phenyl, halo or nitro groups or Z is a substituent having the formula

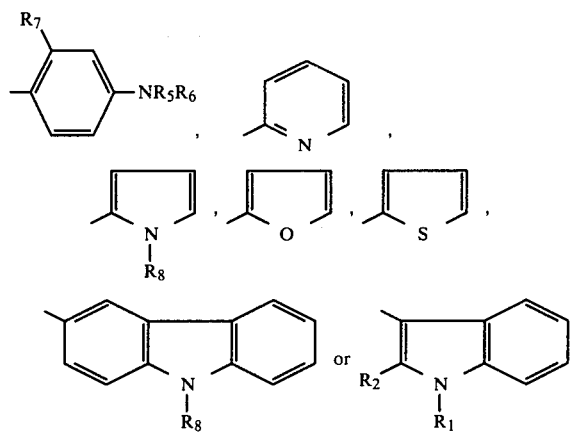

where in the above formulas
R$_5$ and R$_6$ are independently lower-alkyl or benzyl;
R$_7$ is hydrogen, lower-alkyl, lower-alkoxy, halo or di-lower-alkylamino, and
R$_8$ is hydrogen or lower-alkyl.

2. A pressure-sensitive carbonless duplicating system or thermal marking system according to claim 1 wherein Z is a substituent having the formula

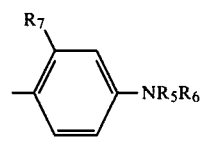

wherein R$_5$, R$_6$ and R$_7$ have the meanings given in claim 1.

3. A pressure-sensitive carbonless duplicating system or thermal marking system according to claim 2 wherein R$_5$ and R$_6$ are each lower-alkyl and R$_7$ is hydrogen.

* * * * *